United States Patent
Seiferlein et al.

(10) Patent No.: US 11,230,162 B2
(45) Date of Patent: Jan. 25, 2022

(54) INTERIOR VENTILATION SYSTEM FOR A MOTOR VEHICLE

(71) Applicant: Bayerische Motoren Werke Aktiengesellschaft, Munich (DE)

(72) Inventors: Mara Seiferlein, Munich (DE); Hendrik Bernau, Dachau (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 55 days.

(21) Appl. No.: 15/868,325

(22) Filed: Jan. 11, 2018

(65) Prior Publication Data

US 2018/0134112 A1    May 17, 2018

Related U.S. Application Data

(63) Continuation of application No. PCT/EP2016/069234, filed on Aug. 12, 2016.

(30) Foreign Application Priority Data

Sep. 25, 2015    (DE) .................... 10 2015 218 474.9

(51) Int. Cl.
    *B60H 1/00*        (2006.01)
    *G01N 33/00*       (2006.01)
    *B60H 1/26*        (2006.01)

(52) U.S. Cl.
    CPC ......... *B60H 1/008* (2013.01); *B60H 1/00792* (2013.01); *B60H 1/00821* (2013.01);
    (Continued)

(58) Field of Classification Search
    CPC .............. B60H 1/008; B60H 1/00792; B60H 1/00821; B60H 1/00849; B60H 1/26; G01N 33/0004
    (Continued)

(56) References Cited

U.S. PATENT DOCUMENTS 5,256,103 A * 10/1993 Abthoff ................ B60H 3/0625
                                                  454/139
5,377,528 A *  1/1995 Dauvergne ......... B60H 1/00792
                                                  165/11.1
(Continued)

FOREIGN PATENT DOCUMENTS

CN    101001767 A    7/2007
CN    101657335 A    2/2010
(Continued)

OTHER PUBLICATIONS

DE102009034633A1 (translation).*
(Continued)

*Primary Examiner* — Allen R. B. Schult
(74) *Attorney, Agent, or Firm* — Crowell & Moring LLP

(57) ABSTRACT

An interior ventilation system for a motor vehicle includes an air measurement chamber, into which outdoor air of the motor vehicle can be fed via an outside air supply line and vehicle interior air of the motor vehicle can be fed via an inside air supply line, air quality sensors for measuring a harmful-substance content in air located in the air measurement chamber, and a measurement air control unit, which is designed to selectively supply outdoor air and/or vehicle interior air to the air measurement chamber. A motor vehicle includes such an interior ventilation system.

10 Claims, 2 Drawing Sheets

(52) U.S. Cl.
CPC .......... B60H 1/00849 (2013.01); B60H 1/26 (2013.01); G01N 33/0063 (2013.01)

(58) Field of Classification Search
USPC .......................................................... 454/75
See application file for complete search history.

(56) References Cited

U.S. PATENT DOCUMENTS

| | | | |
|---|---|---|---|
| 2003/0181158 A1* | 9/2003 | Schell ................... | F24F 3/0442 454/229 |
| 2004/0244392 A1 | 12/2004 | Gilch et al. | |
| 2008/0092742 A1 | 4/2008 | Marra | |
| 2010/0144261 A1 | 6/2010 | Barkie et al. | |
| 2010/0212332 A1 | 8/2010 | Hofhaus et al. | |
| 2012/0015594 A1* | 1/2012 | Yenneti ................ | B60H 1/008 454/75 |
| 2013/0086976 A1 | 4/2013 | Park et al. | |
| 2013/0137355 A1* | 5/2013 | Patti ................... | B60H 1/00792 454/139 |
| 2016/0052363 A1 | 2/2016 | Ostermeier et al. | |
| 2016/0097311 A1* | 4/2016 | Coelho Ferreira ..... | F01N 3/035 422/119 |
| 2017/0355518 A1* | 12/2017 | Zita ..................... | B65D 88/745 |

FOREIGN PATENT DOCUMENTS

| | | |
|---|---|---|
| CN | 101855099 A | 10/2010 |
| CN | 202952794 U | 5/2013 |
| CN | 203221853 U | 10/2013 |
| DE | 197 09 053 A1 | 9/1998 |
| DE | 102 54 496 A1 | 6/2004 |
| DE | 103 16 294 A1 | 11/2004 |
| DE | 10 2005 027 072 A1 | 12/2006 |
| DE | 10 2007 018 571 A1 | 10/2008 |
| DE | 10 2009 034 633 A1 | 1/2011 |
| DE | 10 2011 057 122 A1 | 4/2013 |
| DE | 10 2013 214 071 A1 | 1/2015 |
| JP | 6-48163 A | 2/1994 |

OTHER PUBLICATIONS

International Search Report (PCT/ISA/210) issued in PCT Application No. PCT/EP2016/069234 dated Nov. 10, 2016 with English translation (six pages).
German-language Written Opinion (PCT/ISA/237) issued in PCT Application No. PCT/EP2016/069234 dated Nov. 10, 2016 (five pages).
German-language Office Action issued in counterpart German Application No. 10 2015 218 474.9 dated Apr. 1, 2016 (five pages).
Chinese-language Office Action issued in counterpart Chinese Application No. 201680033866.X dated Oct. 23, 2019 with English translation (15 pages).
Chinese-language Office Action issued in Chinese Application No. 201680033866.X dated Mar. 5, 2020 with English translation (15 pages).
English translation of Chinese Office Action issued in Chinese Application No. 201680033866.X dated Jul. 29, 2020 (seven pages).

* cited by examiner

INTERIOR VENTILATION SYSTEM FOR A MOTOR VEHICLE

CROSS REFERENCE TO RELATED APPLICATIONS

This application is a continuation of PCT International Application No. PCT/EP2016/069234, filed Aug. 12, 2016, which claims priority under 35 U.S.C. § 119 from German Patent Application No. 10 2015 218 474.9, filed Sep. 25, 2015, the entire disclosures of which are herein expressly incorporated by reference.

BACKGROUND AND SUMMARY OF THE INVENTION

The invention concerns an interior ventilation system for a motor vehicle for measuring ambient air and internal air of the vehicle.

A system and a method for the control of odors and/or harmful substances in the interior of the vehicle are known from DE 102 54 496 A1. The system described in this document has some sensors for detecting harmful substances in the interior of the vehicle and in the surroundings of a vehicle.

Such interior ventilation systems are relatively expensive, including owing to the number of sensors required.

It is the object of the invention to provide an interior ventilation system for detecting harmful substances that can be provided less expensively.

This and other objects are achieved with an interior ventilation system according to embodiments of the invention.

According to an exemplary embodiment of the invention, an interior ventilation system for a motor vehicle is provided with an air measurement chamber, into which ambient (outdoor) air of the motor vehicle is delivered via an external air feed line and internal air of the motor vehicle is delivered via an internal air feed line, air quality sensors for measuring a harmful substance content in air located in the air measurement chamber, and a measurement air control device that is adapted to supply the air measurement chamber selectively with ambient air and internal air.

All air quality sensors that are disposed in the air measurement chamber are disposed to be accessible both to the ambient air and to the internal air. This means that owing to the arrangement within a related, bounded spatial volume, each individual air quality sensor that is disposed in the air measurement chamber is accessible both to the ambient air and to the internal air. The exemplary embodiment has the advantage that combined sensors, for example in the form of a combined air quality sensor module, can be purchased less expensively than purchasing all air quality sensors individually. Further, only a single installation space is required and thus only a single ground connection, a single current connection and a single cable loom connection or bus connection, which reduces the cost of assembly. The exemplary embodiment enables all relevant air quality values to be measured centrally.

According to a further exemplary embodiment of the invention, the interior ventilation system includes a PM sensor for measuring a fine dust content in the ambient air, a $NO_x$ sensor for measuring a $NO_x$ content in the ambient air, and a CO sensor for measuring a CO content in the ambient air. The most important air quality values in the ambient air are thereby covered.

According to a further exemplary embodiment of the invention, the interior ventilation system is further provided with an air guidance device that, depending on the setting, takes air for the ventilation of the internal space of the motor vehicle at least predominantly from the surroundings of a vehicle or the interior of the vehicle or stops ventilation of the internal space, and a control device that controls the air guidance device depending on the measurement results of the air quality sensors.

According to a further exemplary embodiment of the invention, the air quality sensors include a $CO_2$ sensor for measuring a $CO_2$ content in the internal air, and the control device is adapted, on exceeding a limit value for the $CO_2$ content, to control the air guidance device so that the air for the ventilation of the internal space is at least predominantly taken from outside of the vehicle. This has the advantage that in air conditioning systems that use $CO_2$ as the coolant, the $CO_2$ sensor can be used as a safety-relevant sensor that can detect a leak in the coolant circuit. Further, an excessive $CO_2$ content in the internal air could result in driver fatigue. This could be avoided by detection and delivering fresh air.

According to a further exemplary embodiment of the invention, the control device is adapted, on exceeding at least one limit value for the fine dust content, $NO_x$ content or CO content, to control the air guidance device so that the air for the ventilation of the internal space is at least predominantly taken from the interior of the vehicle or an air feed is inhibited if the limit value for the $CO_2$ content is exceeded or a screen detector signals a fogged windshield. Thus, safety-relevant aspects are prioritized during ventilation of the internal space.

According to a further exemplary embodiment of the invention, the air measurement chamber is embodied in a housing to which the air quality sensors are attached, wherein the housing has a single interface for connecting to a vehicle bus. This reduces the costs of assembly and cabling.

According to a further exemplary embodiment, the measurement air control device only switches the air quality sensors that are provided for measuring the ambient air to be active if the air measurement chamber is supplied with ambient air, and only switches the air quality sensors that are provided for measuring the internal air to be active if the air measurement chamber is supplied with internal air. Thus, the sensors are only activated when required, which can save energy.

According to a further exemplary embodiment of the invention, the measurement air control device is adapted for controlling air flow control elements that selectively feed air via the external air feed line or the internal air feed line, wherein the air flow control elements include a fan, a pump and/or vacuum generation device.

According to a further exemplary embodiment of the invention, the air quality sensors include a VOC sensor for measuring a content of volatile hydrocarbons in the internal air, and the control device is adapted, on exceeding a limit value for the VOC content, to control the air guidance device so that the air for the ventilation of the internal space is at least predominantly taken from outside of the vehicle.

Moreover, the invention provides a motor vehicle with an interior ventilation system according to any one of the above exemplary embodiments.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 1:
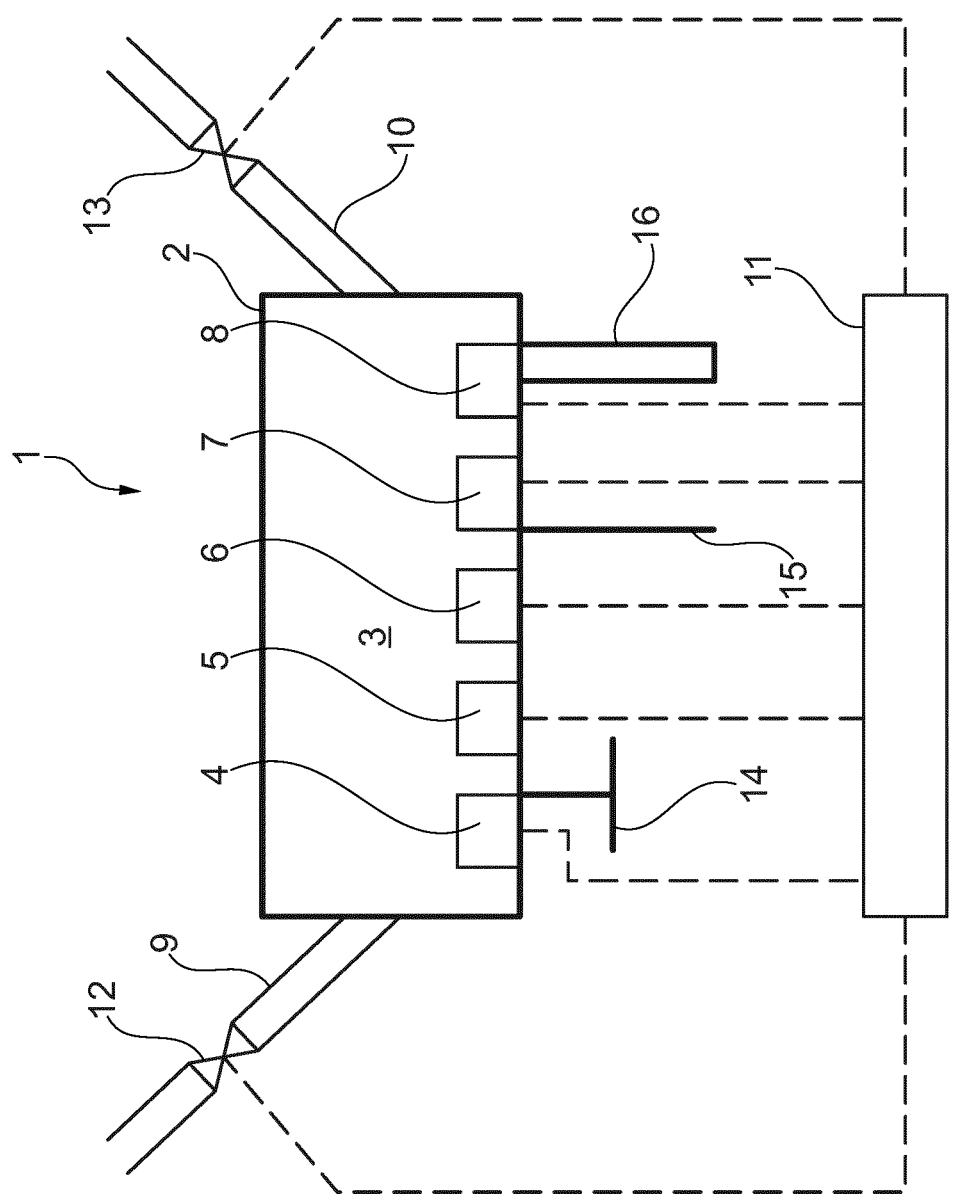
FIG. 1 is a schematic representation of an air quality sensor module according to an embodiment of the invention.

An air quality sensor module 1 is represented schematically in FIG. 1. The module 1 includes a housing 2 in which an air measurement chamber 3 is embodied. A plurality of air quality sensors 4, 5, 6, 7 and 8 is disposed on the housing 2 and connected to the housing so that at least measurement sections thereof protrude into the air measurement chamber 3. Of course, they can also be fully disposed within the housing 2. The air measurement chamber 3 is closed apart from an external air feed line 9, an internal air feed line 10 and an optional outlet (not shown).

Ambient air of a motor vehicle 17 in which the air quality sensor module 1 is mounted can be introduced into the air measurement chamber 3 via the external air feed line 9. Interior air of the motor vehicle 17 can be introduced into the air measurement chamber 3 via the internal air feed line 10. The air measurement chamber 3 thus bounds a related spatial volume, within which every point is accessible to both the ambient air introduced via the external air feed line 9 and to the internal air introduced via the internal air feed line 10, as can be seen from FIG. 1. A significant aspect of the invention is that, unlike the air quality sensors being distributed spaced apart from each other in the vehicle as with the prior art, the sensors are combined and all air quality sensors 4 through 8 that are provided for the detection of harmful substances within the interior ventilation system measure the air in the same air measurement chamber 3. Thus, all air quality sensors 4 through 8 that are provided for detecting harmful substances and that are associated with the air measurement chamber 3 are disposed so that they are accessible both to the ambient air introduced via the external air feed line 9 and to the internal air introduced via the internal air feed line 10. As a result, all air quality sensors 4 through 8 are combined in a housing 2, which in turn only requires a single interface for connecting to a control device of the vehicle and which simplifies mounting in the motor vehicle 17.

Moreover, a measurement air control unit 11 is provided that can include electrical circuits and software. The measurement air control unit 11 is adapted to control air flow control elements 12, 13 that are shown simplified in the form of valves. These elements 12, 13 should however generally include means that are adapted to pass the air flows through the external air feed line 9 and the internal air feed line 10 and/or to inhibit the air flows. Thus, the air flow control elements 12, 13 can, for example, be pumps, fans, valves, flaps, vacuum devices and pressure devices. The function of the air flow control elements 12, 13 is such that the same transport ambient (outside) air into the air measurement chamber 3 or fill the air measurement chamber 3 with ambient air if harmful substances are measured in the ambient air and transport internal air into the air measurement chamber 3 or fill the air measurement chamber 3 with internal air if harmful substances are measured in the internal air. The air that was previously present in the air measurement chamber 3 can either be discharged via an optional outlet or discharged or forced out via the respective feed line 9, 10 that is not used to introduce air. The changeover between measuring ambient air and measuring internal air is actuated by the measurement air control unit and can be carried out alternately or selected by the measurement air control unit 11.

The air quality sensors 4 through 8 are preferably a PM sensor 4 for measuring a fine dust content in the ambient air, a $NO_x$ sensor 5 for measuring a $NO_x$ content in the ambient air, a CO sensor 6 for measuring a CO content in the ambient air, a $CO_2$ sensor 7 for measuring a $CO_2$ content in the internal air, and a VOC sensor 8 for measuring a content of volatile hydrocarbons in the internal air. The PM sensor 4 is preferably adapted to measure a fine dust content of the particle size PM2.5, but it can also be adapted for any other particle size. The PM sensor 4 is preferably an optical sensor. The other air quality sensors 5 through 8 are preferably each provided with a measurement chip to which pastes that are matched to the measuring medium are applied. The operation of the individual air quality sensors 4 through 8 is known from the prior art and therefore is not described further.

Furthermore, the air sensor module 1 has a ground connection 14 and a current connection 15, which for example has a potential of +12V or +5V. Further, an interface 16 for connecting the air sensor module 1 to a vehicle bus is provided. The advantage is that by combining the air quality sensors only a single interface 16 is required for connecting all the air quality sensors 4 through 8. This saves on interfaces, cabling and installation costs.

Figure 2:
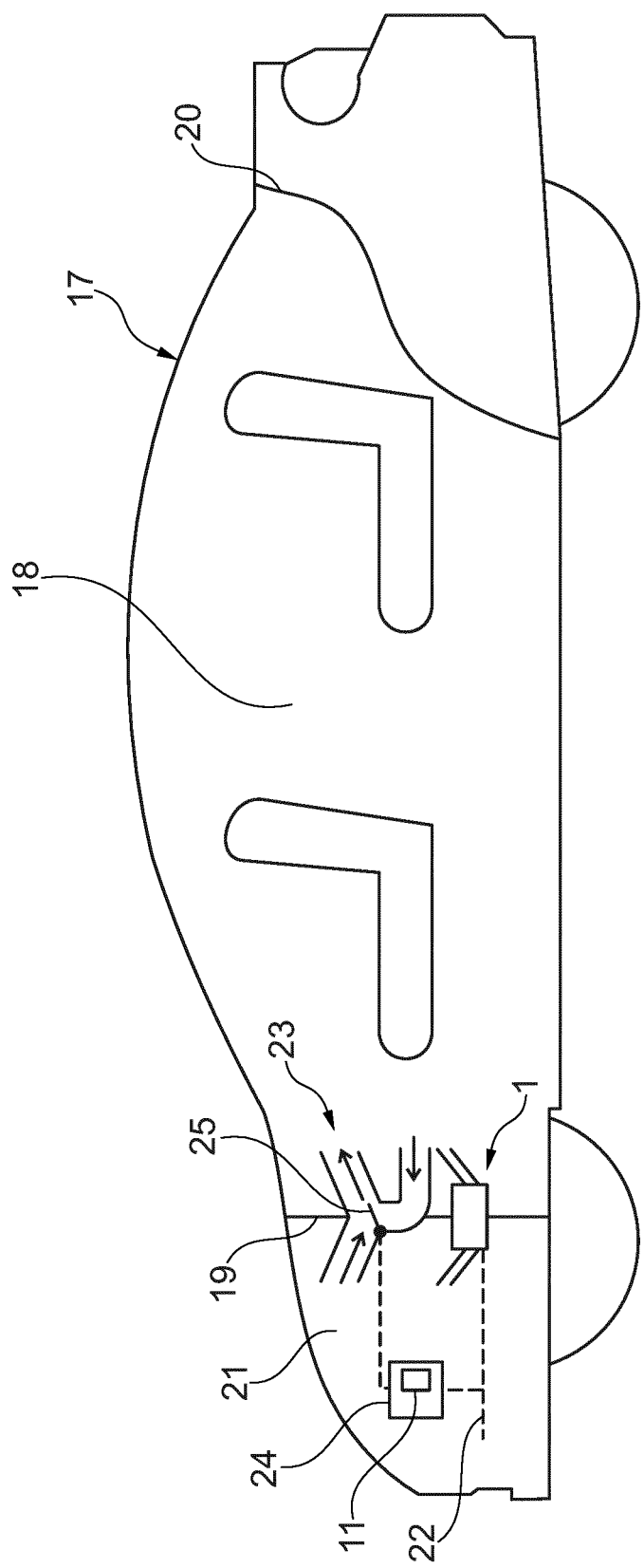
FIG. 2 is a schematic diagram of a motor vehicle with an exemplary interior ventilation system of the invention.

FIG. 2 shows schematically a motor vehicle 17 with a vehicle interior 18 that is bounded at the front by an end wall 19 (also referred to as a bulkhead), especially in the case of an automobile. In the rear, the interior of the vehicle 18 either extends to a trunk of the motor vehicle 17 or is separated from the trunk by a separating wall 20. The air in the interior of the vehicle 18 is referred to in this description as internal air. The air surrounding the vehicle 17 is the ambient (outside) air, which as a rule is also present in an engine compartment 21.

The air sensor module 1 can be mounted in the end wall 19 or in the surroundings thereof. By means of the interface 16, the air sensor module 1 is electrically connected to a vehicle bus 22 (for example CAN, LIN, PWM), which, as is well known, is a data line with parallel lines, wherein the interface 16 is or can be electrically connected to all or at least several of the parallel lines. For communications by the air sensor module 1 with other control elements via the vehicle bus 1, a unique identifier is assigned to the air sensor module 1 that is transmitted via the vehicle bus 22. The interface 16 can also be embodied as a wireless interface and data can be exchanged by way of electromagnetic waves, for example via Bluetooth, WLAN, NFC, etc.

For the ventilation of the interior of the vehicle 18, an air guidance device 23 is provided that is represented in a highly schematic form. It is the function of the air guidance device 23, depending on the setting, to take air for the ventilation of the internal space of the motor vehicle 17 at least predominantly (preferably essentially fully) from the surroundings of the motor vehicle 17 or the vehicle interior 18 of the motor vehicle 17, or to stop the ventilation of the internal space. The air guidance device 23 is actuated by a control device 24 that can include electrical circuits and software, depending on the measurement results of the air quality sensors 4-8 that it obtains from said sensors directly or via the measurement air control unit 11. The control device 24 can contain the measurement air control unit 11; the measurement air control unit 11 can be embodied in the air sensor module 1 or the measurement air control unit 11 can be provided separately. The control device 24 is likewise connected to the vehicle bus 22.

During the operation of the interior ventilation system, besides the wishes of the passenger, who can manually select an air feed for ventilation of the internal space between ambient air feed and internal air circulation, an automatic mode is provided that controls the air guidance device 23 depending on the measurement results of the air quality sensors so that in the event of selection between ambient air and internal air the air is taken from the location where it is less harmful to the human organism. For the purposes of this air guidance, for example an air recirculation flap 25 is provided within the air guidance device 23. For this purpose, the control device 24 is adapted to control the air guidance device so that on exceeding a predetermined limit value for a limit value relating to the ambient air, in particular of the $NO_x$ content, of the CO content and/or of the fine dust content, the air for the ventilation of the internal space of the motor vehicle is at least predominantly (preferably essentially fully) taken from the vehicle interior 18 of the motor vehicle 17 or the ventilation of the internal space is stopped. Further, the control device 24 is adapted to control the air guidance device so that, on exceeding a predetermined limit value for a limit value relating to the internal air, in particular of the VOC content and/or of the $CO_2$ content, the air for the ventilation of the internal space of the motor vehicle is at least predominantly (preferably essentially fully) taken from the surroundings of the motor vehicle 17. If predetermined limit values are exceeded both in the ambient air and in the internal air, then the control device 24 performs a weighting regarding which harmful substances are more harmful or absolutely require a certain air supply. If for example a defined limit value for the $CO_2$ content of the internal air is exceeded, then the air for the ventilation of the internal space of the motor vehicle must be taken from the surroundings of the motor vehicle 17. Likewise, in the event of fogging of the windshield, which for example can be detected by a screen detector, the air for the ventilation of the internal space of the motor vehicle must be taken from the surroundings of the motor vehicle 17.

For the information of the occupants of the vehicle, visual or audible information and/or a warning message can be output that provides information about the determined air quality. For example, exceeding defined air quality limit values can be indicated, and the occupants of the vehicle can be informed about measures that the vehicle is carrying out and/or that the occupants of the vehicle must carry out.

Moreover, the interior ventilation system according to the invention can have an active air purification mechanism that cleans the air by filtering and/or ionization. For this purpose, the air to be fed into the interior of the vehicle is passed through the air purification mechanism.

Whereas the invention has been illustrated and described in detail in the drawings and the preceding description, said illustration and description are to be considered as illustrative or by way of example and not as limiting and are not intended to limit the invention to the disclosed exemplary embodiments. The mere fact that certain features are named in various dependent claims shall not indicate that that a combination of said features could not also be used advantageously.

REFERENCE CHARACTER LIST

1 air quality sensor module
2 housing
3 air measurement chamber
4 PM sensor (air quality sensor)
5 $NO_x$ sensor (air quality sensor)
6 CO sensor (air quality sensor)
7 $CO_2$ sensor (air quality sensor)
8 VOC sensor (air quality sensor)
9 external air feed line
10 internal air feed line
11 measurement air control unit
12 air flow control element
13 air flow control element
14 ground connection
15 current connection
16 interface
17 motor vehicle
18 interior of the vehicle
19 end wall
20 separating wall
21 engine compartment
22 vehicle bus
23 air guidance device
24 control device
25 air recirculation flap The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An interior ventilation system for a motor vehicle, comprising:
    an air guidance device for a vehicle internal space for passengers that, depending on a setting, takes air for ventilation of the internal space at least predominantly from the surroundings of the motor vehicle or from the internal space, or stops the ventilation of the internal space;
    an air measurement chamber, separate from the air guidance device, into which ambient air from surroundings of the motor vehicle is deliverable via an external air feed line and internal air of the motor vehicle is deliverable via an internal air feed line, the external air feed line and the internal air feed line being separate from feed lines of the air guidance device;
    air quality sensors for measuring a harmful substance content in air disposed in a common volume in the air measurement chamber;
    a measurement air control unit that is adapted to automatically selectively supply all of the air quality sensors in the common volume in the air measurement chamber with ambient air or internal air received from the external air feed line and the internal air feed line, respectively; and
    a control device that controls the air guidance device depending on measurement results of the air quality sensors and a comparison of a relative quality of the internal air and the ambient air,
    wherein
        the measurement air control device only switches a first portion of the air quality sensors that are provided for measuring the ambient air to be active if the air measurement chamber is supplied with ambient air, and only switches a second portion of the air quality sensors that are provided for measuring the internal air to be active if the air measurement chamber if supplied with internal air, and at least one of the air quality sensors in at least one of the first and second portions of the air quality sensors is only in the at least one of the first and second portions of the air quality sensors.

2. The interior ventilation system according to claim 1, wherein
the air quality sensors comprise a PM sensor for measuring a fine dust content in the ambient air, a NOx sensor for measuring a NOx content in the ambient air, and a CO sensor for measuring a CO content in the ambient air.

3. The interior ventilation system according to claim 2, wherein
the air quality sensors comprise a $CO_2$ sensor for measuring a $CO_2$ content in the internal air, and
the control device is adapted, on exceeding a limit value for the $CO_2$ content, to control the air guidance device so that the air for the ventilation of the internal space is at least predominantly taken from the surroundings of the vehicle.

4. The interior ventilation system according to claim 3, wherein
the control device is adapted, on exceeding at least one limit value for fine dust content, NOx content or CO content, to control the air guidance device so that the air for the ventilation of the internal space is at least predominantly taken from the interior of the vehicle or an air feed is inhibited if the limit value for the $CO_2$ content is not exceeded or a screen detector signals a fogged windshield.

5. The interior ventilation system according to claim 1, wherein
the air measurement chamber is embodied in a housing to which the air quality sensors are attached, and
the housing comprises a single interface for connecting to a vehicle bus.

6. The interior ventilation system according to claim 1, wherein
the measurement air control device is adapted for controlling air flow control elements, which selectively deliver air via the external air feed line or the internal air feed line, wherein the air flow control elements comprise a fan, a pump and/or a vacuum generator.

7. The interior ventilation system according to claim 1, wherein
the air quality sensors comprise a VOC sensor for measuring a content of volatile hydrocarbons in the internal air, and
the control device is adapted, on exceeding a limit value for the VOC content, to control the air guidance device so that the air for the ventilation of the internal space is at least predominantly taken from the surroundings of the vehicle.

8. The interior ventilation system according to claim 3, wherein
the air quality sensors comprise a VOC sensor for measuring a content of volatile hydrocarbons in the internal air, and
the control device is adapted, on exceeding a limit value for the VOC content, to control the air guidance device so that the air for the ventilation of the internal space is at least predominantly taken from the surroundings of the vehicle.

9. The interior ventilation system according to claim 4, wherein
the air quality sensors comprise a VOC sensor for measuring a content of volatile hydrocarbons in the internal air, and
the control device is adapted, on exceeding a limit value for the VOC content, to control the air guidance device so that the air for the ventilation of the internal space is at least predominantly taken from the surroundings of the vehicle.

10. A motor vehicle comprising an interior ventilation system according to claim 1.

* * * * *